US00PP16382P3

(12) United States Plant Patent
Miyazaki

(10) Patent No.: US PP16,382 P3
(45) Date of Patent: Mar. 28, 2006

(54) ***PHLOX* PLANT NAMED 'SUNPHLO R&W'**

(50) Latin Name: *Phlox drummondii*
Varietal Denomination: Sunphlo R&W

(75) Inventor: Kiyoshi Miyazaki, Hikone (JP)

(73) Assignee: Suntory Flowers Limited, Tokyo (JP)

( * ) Notice: Subject to any disclaimer, the term of this patent is extended or adjusted under 35 U.S.C. 154(b) by 155 days.

(21) Appl. No.: 10/897,373

(22) Filed: Jul. 22, 2004

(65) Prior Publication Data

US 2006/0021101 P1 Jan. 26, 2006

(51) Int. Cl.
*A01H 5/00* (2006.01)

(52) U.S. Cl. ..... Plt./320
(58) Field of Classification Search ..... Plt./320
See application file for complete search history.

(56) References Cited

FOREIGN PATENT DOCUMENTS

JP PBR 6829 10/1998

OTHER PUBLICATIONS

UPOV ROM GTITM Computer Database, GTI Jouve Retrieval Software 2004/06 Citation for 'Sunphlo R&W'.*

Catalog: Takii Seed Co., 2002–2003, 4 pages (with partial translation of p. 3) (also see Information List).

Catalog: Sakata Seed Co., 2000, 3 pages (with partial translation of p. 3) (also see Information List).

Information List.

* cited by examiner

*Primary Examiner*—Howard J. Locker
*Assistant Examiner*—W. C. Haas
(74) *Attorney, Agent, or Firm*—Christie, Parker & Hale, LLP

(57) ABSTRACT

Disclosed herein is a new and distinct variety of *Phlox* plant having an ascending habit and low plant height. The *Phlox* plant has abundant branching, and great profusion of blooms, the whole plant remaining in bloom for a considerable period of time. The flowers are single, the upper side color of the corolla is light purplish pink and yellowish white at the center with strong reddish purple eye. The under side color of the corolla is pale purplish pink and the outside of the corolla tube is pale purplish pink. The plant exhibits a high tolerance to heat and resistance to disease.

2 Drawing Sheets

Botanical designation: *Phlox drummondii.*
Variety denomination: 'Sunphlo R&W'.

BACKGROUND OF THE VARIETY

The present invention relates to a new and distinct variety of *Phlox* plant originated from the crossing of a *Phlox* variety called '9Ph-17' (♀) with a commercial cultivar 'Palona Rose with eye' (unpatented) (♂).

*Phlox* are mainly late spring or summer flowering annuals or perennial, grown for terminal panicles or for a profusion of brightly colored flowers. However, there are only a few *Phlox* which can survive a hot and humid summer and can bloom continuously until autumn. Accordingly, this invention was aimed at obtaining a new variety having vivid reddish purple colored petals, together with good heat tolerance and longer a flowering period.

The female parent '9Ph-17' (unpatented) is a variety having a vigorous growth habit, abundant branching and good heat tolerance.

The male parent 'Palona Rose with eye' (PVP No.8900050 in United States) is a commercial cultivar.

In May 1999, crossing of a breeding line called '9Ph-17' as female parent with a cultivar 'Palona Rose with eye' as pollen parent was conducted at Yokaichi-shi, Shiga-ken, Japan. In January 2000, 50 seedlings were obtained from the crossing. The seedlings were grown in pots and tested, and then a single seedling was selected in view of the flower color, the good heat tolerance and a longer flowering period. The seedling was propagated by cutting and tested by flower potting and bedding from April 2001, at Yokaichi-shi, Shiga-ken, Japan. The botanical characteristics of the plant were then examined using a similar variety, 'Dolly Rose', for comparison. As a result, it was concluded that the *Phlox* plant is distinguishable from any other variety whose existence is known to us and is uniform and stable in its characteristics. The new variety of *Phlox* plant was named 'Sunphlo R&W'.

In the following description, the color information is in accordance with The R.H.S. Colour Chart of The Royal Horticultural Society, London, England.

SUMMARY OF THE VARIETY

This new variety is unlike any *Phlox* commercially available, known to the inventors, as evidenced by the following unique combinations of characteristics.

1. Ascending habit with short stem.
2. Having abundant branching with many blooms.
3. The flowers are single. The petal color is purplish pink (R.H.S.65B) and yellowish white (R.H.S.155B) at the center, with strong reddish purple (R.H.S.72B) eye.
4. The plant has a good tolerance to rain and heat.

The new variety 'Sunphlo R&W' differs from the male parent variety 'Palona Rose with eye' (unpatented) in the following points.

1. The stem color of 'Sunphlo R&W' is dark red (R.H.S.183A). That of 'Palona Rose with eye' is light yellow green (R.H.S.154D).

2. The number of primary branches of 'Sunphlo R&W' more than that of 'Palona Rose with eye'.
3. The base color of corolla of 'Sunphlo R&W' is light purplish pink (R.H.S.65B). That of 'Palona Rose with eye' is vivid purplish red (R.H.S.67B).
4. The heat tolerance of 'Sunphlo R&W' is strong. That of 'Palona Rose with eye' is weak.

The new variety 'Sunphlo R&W' differs from the similar variety 'Dolly Rose' (unpatented) in the following points.

1. The stem color of 'Sunphlo R&W' is dark red (R.H.S.183A). That of 'Dolly Rose' is light yellow green (R.H.S.154D).
2. The diameter of corolla of 'Sunphlo R&W' is larger than that of 'Dolly Rose'.
3. The petal of 'Sunphlo R&W' is broader than that of 'Dolly Rose'.
4. The color of corolla-upper side of 'Sunphlo R&W' is light purplish pink (R.H.S.65B). That of 'Dolly Rose' is deep purplish pink (R.H.S.66C).
5. The eye color of 'Sunphlo R&W' is strong reddish purple (R.H.S.72B). That of 'Dolly Rose' is vivid red (R.H.S.57B).
6. The heat tolerance of 'Sunphlo R&W' is stronger than 'Dolly Rose'.

The new variety of *Phlox* plant 'Sunphlo R&W' was asexually reproduced by the use of cuttings at Yokaichi-shi, Shiga-ken, Japan, and the homogeneity and the stability thereof were confirmed.

The instant plant retains its distinctive characteristics and reproduces true to type in successive generations.

BRIEF DESCRIPTION OF THE PHOTOGRAPH

The accompanying photographs show, as nearly true as it is reasonably possible to make the same in color illustrations of this character, typical specimens of the new cultivar. The depicted plants had been reproduced by the use of cuttings and were photographed June 2002 while growing outdoors in 20 cm pots at an age of approximately 3 months at Yokaichi-shi, Shiga-ken, Japan.

DESCRIPTION OF THE NEW VARIETY

Figure 1:
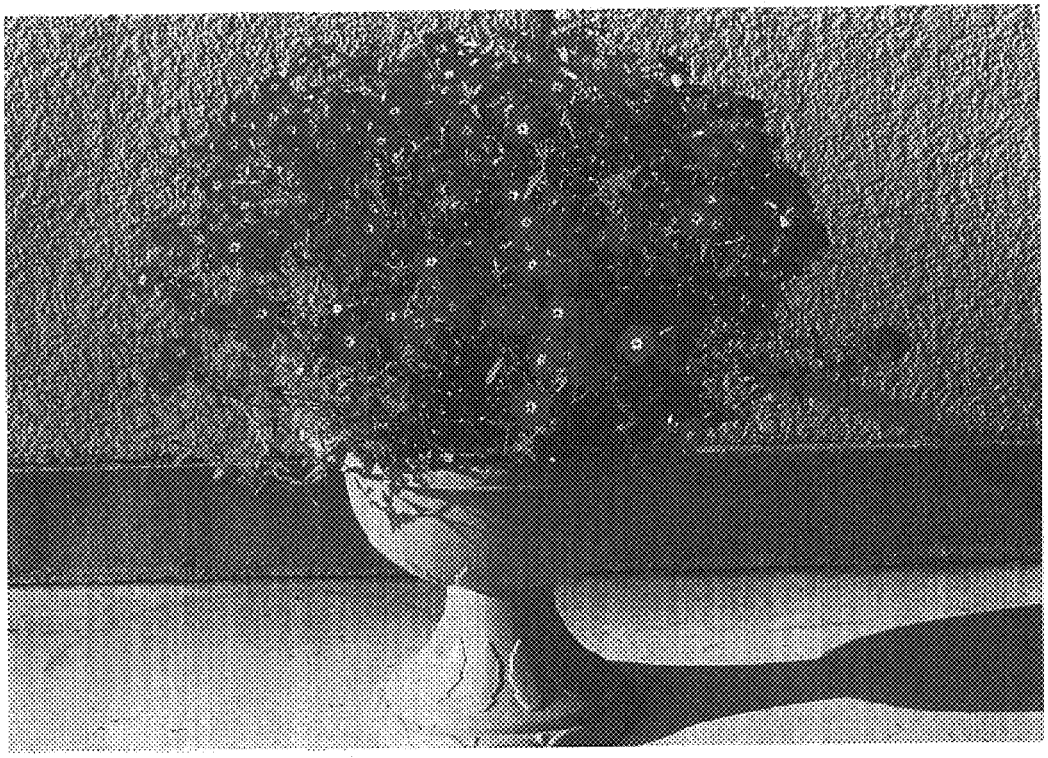
FIG. 1 illustrates an entire plant of the new variety while growing in a pot.
Figure 2:
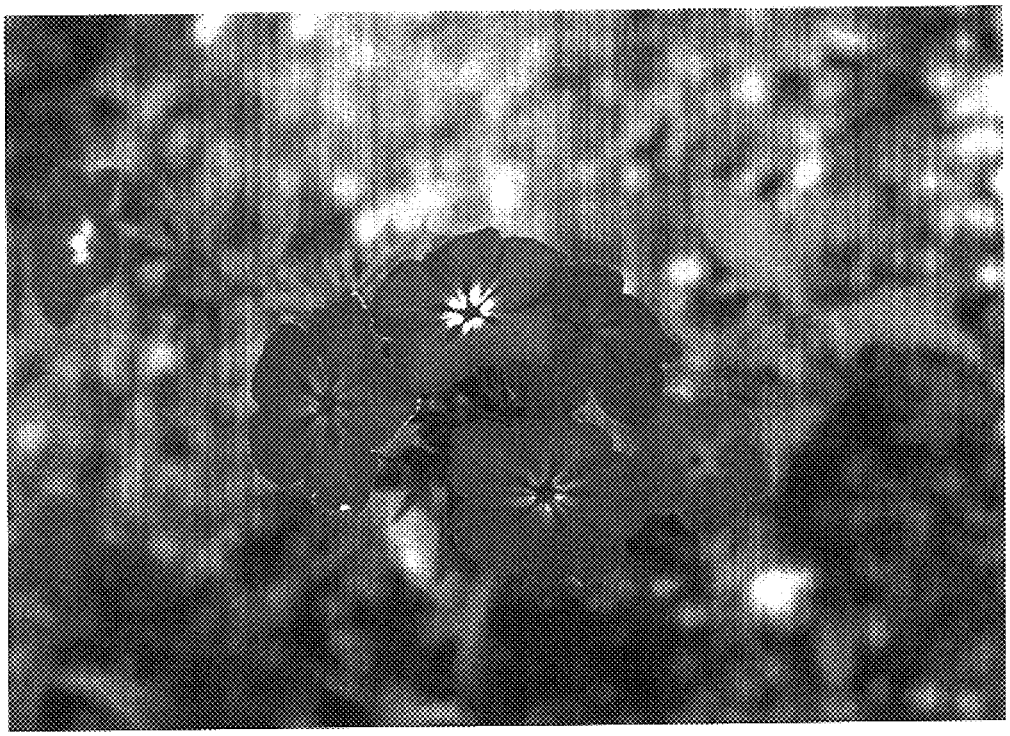
FIG. 2 illustrates a close view of the foliage and blossoms of the new variety.

The botanical characteristics of the new and distinct variety of *Phlox* plant named 'Sunphlo R&W' are set forth hereafter. The plants were observed as grown in typical outdoor conditions during June 2002 at Yokaichi-shi, Shiga-ken, Japan, at an age of approximately 3 months. The average day temperature is approximately 22° C. and the average night temperature is approximately 12° C.

Plant:

*Growth habit.*—Ascending.
*Plant height.*—Approximately 14 cm.
*Spreading area of plant.*—Approximately 32 cm.
*Blooming period.*—Early April to late October in the southern Kanto area, Japan. A typical flower commonly lasts approximately 5 days on the plant when experiencing a temperature of approximately 20° C.

Stem:

*Diameter.*—Approximately 1.7 mm.
*Pubescence.*—Present and typical of the species.
*Primary branching.*—Abundant.
*Internode length.*—Approximately 11.0 mm.
*Color.*—R.H.S. 183A (greyed-purple group).

Leaf:

*Phyllotaxis.*—Alternate.
*Whole shape.*—Lanceolate. The apex shape is acute, and the base shape is obtuse. The leaf margin shape is entire.
*Length.*—Approximately 4.0 cm.
*Width.*—Approximately 1.0 cm.
*Color.*—Upper side color is R.H.S. 146A (yellow-green group). Under side color is R.H.S. 146A (yellow-green group).
*Thickness.*—Approximately 0.3 mm.
*Pubescence.*—Present at upper side and under side.

Flower:

*Inflorescence.*—Cyme.
*Inflorescence length.*—Approximately 4.5 cm.
*Inflorescence width.*—Approximately 7.0 cm.
*Flower shape.*—Salverform.
*Corolla shape.*—Orbicular.
*Flower diameter.*—Approximately 2.8 cm.
*Flower depth.*—Approximately 1.5 cm.
*Petal width.*—Approximately 1.3 cm.
*Petal length from throat.*—Approximately 1.2 cm.
*Apex shape.*—Rounded cuspidate.
*Number of petal.*—5.
*Margin.*—Entire.
*Corolla tube diameter.*—Approximately 1.5 mm.
*Length of corolla tube.*—Approximately 1.5 cm.
*Upper petal surface color.*—Near R.H.S. 65B.
*Lower petal surface color.*—Near R.H.S. 62D.
*Upper petal surface color* (*near the throat*).—Near R.H.S. 155B.
*Petal eye color* (*central upper surface*).—Near R.H.S. 72B.
*Outside color of corolla tube.*—R.H.S. 62D (red-purple group).
*Reproductive organs.*—1 normal pistil and 5 normal stamens. Color of pistil is R.H.S. 155B (white group). Color of stamen is R.H.S. 6B (yellow group).
*Pedicel.*—Approximately 1.0 mm in diameter and Approximately 0.6 cm in length. Color of pedicel is near R.H.S. 146A.
*Calyx.*—Campanulate, 5 sepals fused at the base. Sepal length is approximately 5.5 mm, width is approximately 1.0 mm. Sepal shape is lanceolate. Sepal margins are entire. Upper and lower sepal surface color is near R.H.S. 146A.

The plant grows well at temperatures up to 30° C.

Seed production has not been observed.

The lower and upper temperatures for the plant survival have not been evaluated. Disease resistance to pathogens common to *Phlox* has not been observed.

This new variety of *Phlox* plant is most suitable for flower bedding and potting. It is unnecessary to pinch of old blossoms to enhance the formation of new blossoms.

It is claimed:

1. A new and distinct variety of *Phlox* plant named 'Sunphlo R&W', substantially as herein illustrated and described.

* * * * *